US009535023B2

(12) United States Patent
Ghesquiere et al.

(10) Patent No.: US 9,535,023 B2
(45) Date of Patent: *Jan. 3, 2017

(54) ANALYTE TEST SENSOR AND METHOD OF MANUFACTURING THE SAME

(71) Applicant: Abbott Diabetes Care Inc., Alameda, CA (US)

(72) Inventors: Alexander G. Ghesquiere, Potomac, MD (US); Simon Tonks, Abingdon (GB)

(73) Assignee: Abbott Diabetes Care Inc., Alameda, CA (US)

( * ) Notice: Subject to any disclaimer, the term of this patent is extended or adjusted under 35 U.S.C. 154(b) by 322 days.

This patent is subject to a terminal disclaimer.

(21) Appl. No.: 14/487,844

(22) Filed: Sep. 16, 2014

(65) Prior Publication Data

US 2015/0002171 A1    Jan. 1, 2015

Related U.S. Application Data

(60) Continuation of application No. 12/176,066, filed on Jul. 18, 2008, now Pat. No. 8,834,690, which is a
(Continued)

(51) Int. Cl.
*G01N 27/04* (2006.01)
*C12Q 1/00* (2006.01)
(Continued)

(52) U.S. Cl.
CPC ............... *G01N 27/04* (2013.01); *C12Q 1/001* (2013.01); *G01N 27/3274* (2013.01); *G01N 31/00* (2013.01); *G01N 27/4175* (2013.01)

(58) Field of Classification Search
None
See application file for complete search history.

(56) References Cited

U.S. PATENT DOCUMENTS 4,005,002 A    1/1977   Racine et al.
4,062,750 A    12/1977  Butler
(Continued)

FOREIGN PATENT DOCUMENTS

GB    2337122    11/1999
GB    2351153    12/2000
(Continued)

*Primary Examiner* — Luan Van
*Assistant Examiner* — Steven E Rosenwald
(74) *Attorney, Agent, or Firm* — Edward J. Baba; Bozicevic, Field & Francis LLP

(57) ABSTRACT

An analyte test sensor for use in measuring the concentration of a particular analyte in a test sample includes a non-conductive substrate, a reference electrode deposited on the substrate, a working electrode deposited on the substrate and a compensation electrode deposited on the substrate. The compensation electrode is provided with a resistive ladder and is designed to correct for test result inaccuracies which are the result of variances in the manufacturing of the test sensor. Specifically, in one embodiment, the compensation electrode corrects for test result inaccuracies in an analog manner by shunting a portion of the working current away from working electrode. In another embodiment, the compensation electrode corrects for test result inaccuracies in a digital manner by providing a calibration code which is proportional its resistance value. A batch of analyte test sensors are preferably manufactured in the following manner. An initial batch of the test sensors is constructed. Then, a limited sampling of the sensors is tested for accuracy using a control sample. Based on the test results, the resistance value of the compensation electrode for each remaining sensor in the batch is adjusted accordingly.

6 Claims, 4 Drawing Sheets

Related U.S. Application Data division of application No. 11/025,691, filed on Dec. 29, 2004, now Pat. No. 7,418,285.

(51) Int. Cl.
*G01N 27/327* (2006.01)
*G01N 31/00* (2006.01)
*G01N 27/417* (2006.01)

(56) References Cited

U.S. PATENT DOCUMENTS

| | | |
|---|---|---|
| 5,160,278 A | 11/1992 | Johnson |
| 5,312,590 A | 5/1994 | Gunasingham |
| 5,494,562 A | 2/1996 | Maley et al. |
| 5,582,698 A | 12/1996 | Flaherty et al. |
| 5,628,890 A | 5/1997 | Carter et al. |
| 5,707,502 A | 1/1998 | McCaffrey et al. |
| 5,741,634 A | 4/1998 | Nozoe et al. |
| 6,540,891 B1 | 4/2003 | Stewart et al. |
| 6,730,200 B1 | 5/2004 | Stewart et al. |
| 6,814,844 B2 | 11/2004 | Bhullar et al. |
| 7,968,058 B2 * | 6/2011 | Beaty ............... B01L 3/545 204/400 |
| 8,834,690 B2 * | 9/2014 | Ghesquiere ........ G01N 27/3274 204/401 |
| 2004/0094433 A1 | 5/2004 | Neel et al. |
| 2004/0106190 A1 | 6/2004 | Yang et al. |
| 2004/0124098 A1 * | 7/2004 | Huang ............... G01N 27/3273 205/775 |
| 2004/0244151 A1 * | 12/2004 | Sakata ............ G01N 33/48771 23/306 |
| 2005/0023137 A1 | 2/2005 | Bhullar et al. |
| 2005/0023152 A1 | 2/2005 | Surridge et al. |
| 2005/0279647 A1 | 12/2005 | Beaty |

FOREIGN PATENT DOCUMENTS

| | | |
|---|---|---|
| WO | 91/09139 | 6/1991 |
| WO | 99/13099 | 3/1999 |
| WO | 99/13101 | 3/1999 |
| WO | 03/050534 | 6/2003 |

* cited by examiner

ANALYTE TEST SENSOR AND METHOD OF MANUFACTURING THE SAME

CROSS-REFERENCE TO RELATED APPLICATIONS

This application is a continuation of U.S. patent application Ser. No. 12/176,066, filed on Jul. 18, 2008, which is a divisional of U.S. patent application Ser. No. 11/025,691, filed Dec. 29, 2004, now U.S. Pat. No. 7,418,285, the disclosures of which are herein incorporated by reference.

BACKGROUND OF THE INVENTION

The present invention relates generally to test sensors and more particularly to electrochemical test sensors.

There are many medical conditions which require frequent measurement of the concentration of a particular analyte in the blood of a patient. For example, diabetes is a disease which typically requires a patient to routinely measure the concentration of glucose in his/her blood. Based upon the results of each blood glucose measurement, the patient may then require a particular drug treatment (e.g., an injection of insulin) in order to regulate that the blood glucose level of the patient remains within a specified range. Exceeding the upper limit of said range (hyperglycemia) or dropping beneath the lower limit of said range (hypoglycemia) should be avoided with as much diligence as possible to prevent the patient from experiencing serious medical complications which include, inter alia, retinopathy, nephropathy, and neuropathy.

A multi-step process is commonly practiced by diabetes patients to self-monitor the level of glucose present in their blood.

In the first step of said process, a patient is required to provide a blood sample suitable for testing. Blood samples taken from a patient for blood sugar monitoring are typically obtained by piercing the skin of the patient using a lancing device. A lancing device typically includes a body and a lancet. The body is typically adapted to be held by the user, the lancet being coupled to the body and being adapted to penetrate through the epidermis (the outermost layer of the skin) of the patient and into the dermis (the layer of skin directly beneath the epidermis) which is replete with capillary beds. The puncture of one or more capillaries by the lancet generates a sample of blood which exits through the incision in the patient's skin.

In some lancing devices, the lancet extends from the body at all times. In other lancing devices, the lancet is adapted to be moved, when actuated, from a retracted position in which the lancet tip is disposed within the body to an extended position in which the lancet tip extends beyond the body. Typically, the movement of the lancet from its retracted position to its extended position is effected with such force that contact of the moving lancet tip with the skin of a patient results in the piercing of the skin of the patient. In many such lancing devices having a movable lancet, the lancet is automatically drawn back into the body after reaching its extended position (e.g., using a spring) in order to minimize the risk of inadvertent lancet sticks.

In the second step of said process, a blood glucose monitoring system is utilized to measure the concentration of glucose in the blood sample. One type of glucose monitoring system which is well known and widely used in the art includes a blood glucose meter (also commonly referred to as a blood glucose monitor) and a plurality of individual, disposable, electrochemical test sensors which can be removably loaded into the meter. Examples of blood glucose monitoring systems of this type are manufactured and sold by Abbott Laboratories of Abbott Park, Ill. under the PRECISION line of blood glucose monitoring systems.

Each individual electrochemical test sensor (also commonly referred to as an electrochemical test strip) typically includes a substrate which is formed as a thin, rectangular strip of non-conductive material, such as plastic. A plurality of carbon-layer electrodes are deposited (e.g., screen printed) on the substrate along a portion of its length in a spaced apart relationship, one electrode serving as the reference electrode for the test sensor and another electrode serving as the working electrode for the test sensor. All of the conductive electrodes terminate at their first ends to form a reaction area for the test sensor. In the reaction area, an enzyme is applied onto the first end of the working electrode. When exposed to the enzyme, glucose present in a blood sample undergoes a chemical reaction which produces a measurable electrical response (i.e., a current). The second ends of the electrodes are disposed to electrically contact associated conductors located in the blood glucose monitor, as will be described further below.

A blood glucose monitor is typically modular and portable in construction to facilitate its frequent handling by the patient. A blood glucose monitor often comprises a multifunction test port which is adapted to receive the test sensor in such a manner so that an electrical communication path is established between the second ends of the test strip electrodes and the electronic circuitry for the blood glucose monitor. Within the housing of the monitor, the test port is electrically connected to a microprocessor which controls the basic operations of the monitor. The microprocessor, in turn, is electrically connected to a memory device which is capable of storing a multiplicity of blood glucose test results.

In use, the blood glucose monitoring system of the type described above can be used in the following manner to measure the glucose level of a blood sample and, in turn, store the result of said measurement into memory as test data. Specifically, a disposable electrochemical test sensor is unwrapped from its packaging and is inserted into the test port of the monitor. With the test sensor properly inserted into the monitor, there is established a direct electrical contact between the second ends of the electrodes of the test sensor and the conductors contained within the test port, thereby establishing an electrical communication path between the test sensor and the monitor. Having properly disposed the test sensor into the test port, the monitor applies a voltage (e.g., 200 mv) across the second ends of the electrodes and automatically provides a "ready" indication on its display.

The user is then required to provide a blood sample using a lancing device. Specifically, a disposable lancet is unwrapped from its protective packaging and is loaded into a corresponding lancing device. The lancing device is then fired into the skin of the patient to provide a blood sample.

After lancing the skin, the patient is required to deposit one or more drops of blood from the patient's wound site onto the reaction area of the test sensor, the blood sample creating a conductive path between the first ends of the working and reference electrodes. When a sufficient quantity of blood is deposited on the reaction area of the test sensor, an electrochemical reaction occurs between glucose in the blood sample and the enzyme deposited on the first end of the working electrode which, in turn, produces an electrical current which decays exponentially over time. It should be noted that the value of this electrical current, which is commonly referred to in the art as the working current, is proportional to the concentration of glucose in the blood sample.

The decaying electrical current created through the chemical reaction between the enzyme and the glucose molecules in the blood sample travels along the working electrode and is measured by a current measuring device located within the monitor. The microprocessor of the monitor, which is connected to the current measuring device, correlates the measured working current into a standard numerical glucose value (e.g., using a scaling factor). The numerical glucose value calculated by the monitor is then shown on the monitor display for the patient to observe. In addition, the data associated with the particular blood glucose measurement is stored into memory.

Electrochemical test strips of the type described above are conventionally manufactured in batches. Due to inevitable inconsistencies in manufacturing, variances often arise between different batches of test strips (e.g., the size of the working and reference electrodes, the amount of enzyme deposited on the working electrode, etc.). These manufacturing variances have been found to directly alter the value of the working current produced when a blood sample is deposited on the test strip. As can be appreciated, any alteration of the value of the measured working current can render the glucose level reading calculated therefrom potentially inaccurate, which is highly undesirable.

Accordingly, there presently exist different methods for adjusting the value of the measured working current to compensate for such variances in manufacturing.

For example, in one well known adjustment method, an independent calibration strip is utilized to provide information relating to a batch of test strips to the blood glucose meter. Specifically, a batch of test strips is manufactured and then, in a subsequent step, a limited sampling of the test strips is tested for accuracy by the manufacturer using a blood sample of a known glucose level. Any deviation in the value of the working current generated from a test strip during this test is used to adjust the results obtained from future tests using the remaining test strips from the same batch. This adjustment is accomplished using an independent calibration strip which contains information relating to the deviation associated with the batch.

In use, a blood glucose meter is provided with a default calibration value. Prior to performing an assay, the separate calibration strip is inserted into the test port of the blood glucose meter. Information provided on the calibration strip is digitally transferred to the microprocessor which, in turn, adjusts the default calibration value for the meter. The adjusted calibration value is then used by the meter to correct future glucose readings which are taken using test strips from the same batch. For example, the calibration strip is often provided with a code which the blood glucose meter then converts to a particular numerical value. This numerical value is then utilized by the microprocessor to convert the working current from its measured (i.e., inaccurate) value to a compensated (i.e., true) value. The compensated value of the working current is then utilized by the meter to calculate an accurate blood glucose concentration reading. It should be noted that the particular code associated with a batch of test strips is often stored in memory on the calibration strip using at least one of the following means: a resistor, read only memory (ROM), a key code or a barcode.

The above-described use of an independent calibration strip to digitally calibrate a blood glucose meter prior to testing introduces some notable drawbacks. First, the use of an independent calibration strip requires a patient to perform the time-consuming and complicated task of digitally calibrating a blood glucose meter prior to performing an assay using a test strip from its associated batch. Second, the use of an independent calibration strip in conjunction with a batch of test strips significantly increases the overall manufacturing costs for said batch, this increase in manufacturing costs being a direct consequence of the costly memory requirement for the calibration strip.

Accordingly, in a second well-known adjustment method, calibration information is provided directly on each test strip in a particular batch (the calibration information, in turn, is used by the meter to digitally adjust the measured working current to its compensated, or actual, value). As an example, one well-known test strip utilizes a plurality of contact pads which can be interconnected in a particular pattern so as to represent a specific calibration code. Specifically, the test strip is manufactured with six isolated test pads which are interconnected through a series of conductive leads. After the batch of test strips has been manufactured, a sampling of the test strips is tested to determine whether manufacturing tolerances have introduced any inaccuracies. Based on the results of the testing, the manufacturer, in a subsequent step, cuts selected leads (e.g., using a laser) on each remaining test strip in the batch so as to interconnect the conductive pads into a particular pattern.

As such, when the user wishes to perform an assay, a reconfigured test strip is inserted into a compatible blood glucose meter. The meter reads the pattern of interconnected pads on the test strip and, in turn, corresponds said pattern into a particular calibration code. The meter then uses the calibration code to digitally convert the working current received during an assay to a compensated (i.e., true) value which can then be used to accurately calculate the blood glucose concentration of the sample.

One drawback associated with the aforementioned test strip is the limited number of calibration codes that it can accommodate. Specifically, the limited number of pads (as well as the limited number of leads) allows for the creation of a minimal number of patterns (typically no more than 10-15 patterns). As a result, only a small number of different calibration codes can be provided for such a test strip. However, it has been found that manufacturing tolerances often require a relatively large number of different calibration codes (e.g., often as many as 50 calibration codes are required). Consequently, the limited number of calibration codes afforded by such a test strip has been found to be inadequate.

SUMMARY OF THE INVENTION

It is an object of the present invention to provide a novel test sensor.

It is another object of the present invention to provide a novel test sensor which undergoes a chemical reaction when exposed to a particular analyte in a test sample, the chemical reaction producing a measurable electrical response which is proportional to the concentration of the analyte in the test sample.

It is yet another object of the present invention to provide a test sensor of the type described above which is provided with means to compensate for manufacturing variances that can compromise the accuracy of its test results.

It is still another object of the present invention to provide a test sensor of the type described above which has a limited number of parts, which is inexpensive to manufacture and which is easy to use.

Therefore, according to one feature of the present invention, there is provided an analyte test sensor for use in measuring the concentration of a particular analyte in a test sample, the analyte test sensor comprising a non-conductive substrate, a reference electrode deposited on the substrate, the reference electrode comprising a first end and a second end, a working electrode deposited on the substrate in a spaced apart relationship from the reference electrode, the working electrode comprising a first end and a second end, an enzyme deposited on the working electrode, the enzyme generating a first current when exposed to the analyte in the test sample, the value of the first current being proportional to the concentration of the analyte in the test sample, and a compensation electrode deposited on the substrate, the compensation electrode comprising a first end and a second end, wherein the compensation electrode is designed to correct test result inaccuracies which are the result of variances in the manufacturing of the analyte test sensor.

According to another feature of the present invention, there is provided a method of manufacturing a common batch of analyte test sensors, wherein each test sensor can be used to measure the concentration of a particular analyte in a test sample, the method comprising the steps of providing a common batch of analyte test sensors, each analyte test sensor comprising a non-conductive substrate, a reference electrode deposited on the substrate, a working electrode deposited on the substrate in a spaced apart relationship from the reference electrode and a compensation electrode deposited on the substrate, the compensation electrode having a resistance value, testing at least one analyte test sensor from the common batch using a test sample which has a known concentration of the particular analyte, the testing step yielding a first set of test results, analyzing the first set of test results to determine the accuracy of the at least one analyte test sensor, and adjusting the resistance value of the compensation electrode for each remaining test sensor in the common batch based upon the test results yielded in the testing step.

Various other features and advantages will appear from the description to follow. In the description, reference is made to the accompanying drawings which form a part thereof, and in which is shown by way of illustration, various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF THE PREFERRED EMBODIMENT

Figure 1:
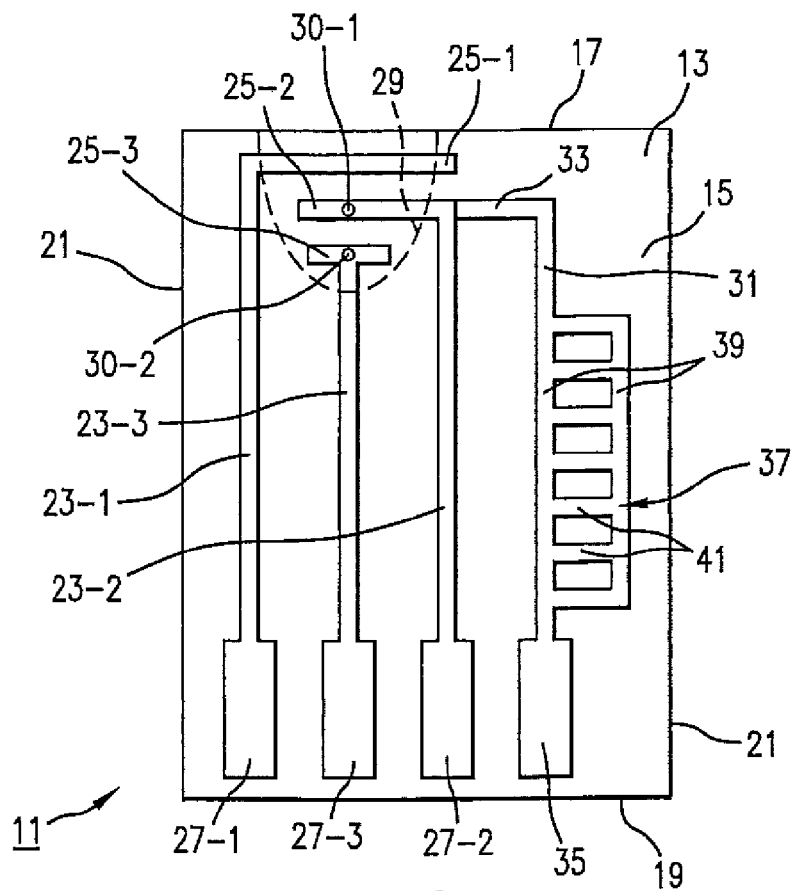
FIG. 1 is a top plan view of a first embodiment of a test sensor constructed according to the teachings of the present invention.
Figure 2:
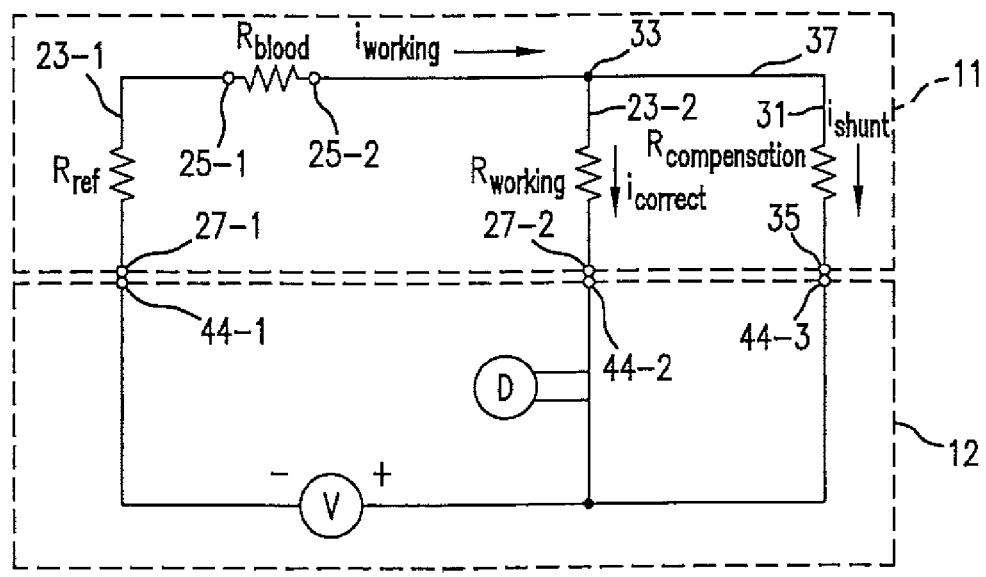
FIG. 2 is a simplified electrical schematic of the test sensor shown in FIG. 1 installed into a first embodiment of a compatible blood glucose meter, the test sensor and the meter together operating to measure the concentration of a particular analyte in a test sample, wherein inaccuracies in the test results which are caused from variances in manufacturing the test strip are compensated for in an analog manner.

Referring now to the drawings, there is shown in FIGS. 1 and 2 a first embodiment of an electrochemical test sensor that is constructed according to the teachings of the present invention, the electrochemical test sensor being identified generally by reference numeral 11. In use, test sensor 11 can be used, in conjunction with a compatible analyte test meter 12, to calculate the concentration of a particular analyte in a test sample. Furthermore, as a principal feature of the present invention, test sensor 11 is provided with means for correcting test result inaccuracies which are the result of common variances in manufacturing, as will be described further below.

As seen most clearly in FIG. 1, test sensor 11 (also referred to herein as test strip 11) includes a unitary, non-conductive substrate 13 which is preferably constructed of plastic using conventional molding techniques. Substrate 13 is preferably formed into a rectangular strip which includes a substantially flat top surface 15, a substantially flat bottom surface (not shown), a front edge 17, a back edge 19 and a pair of side edges 21.

A pair of electrodes 23-1 and 23-2 are deposited onto top surface 15 of substrate 13 along a portion of its length in a spaced-apart relationship, electrode 23-1 serving as the reference electrode for test sensor 13 and electrode 23-2 serving as the working electrode for test sensor 13. An optional third electrode 23-3 may be provided which serves as the trigger electrode for test sensor 11 (i.e., an electrode which measures whether an adequate amount of test sample has been deposited within the reactive area for test sensor 11 to function properly).

Electrodes 23-1, 23-2 and 23-3 are deposited onto substrate 15 in any conventional manner (e.g., screen printing). Electrodes 23-1, 23-2 and 23-3 include a first end 25-1, 25-2 and 25-3, respectively, and a second end 27-1, 27-2 and 27-3, respectively. Preferably, each of electrodes 23-1, 23-2 and 23-3 is constructed out of a carbon-based material. However, due to the inherently high resistance of carbon, a silver (or silver/chloride) layer may be printed over the carbon layer to reduce the resistance of each of electrodes 23-1, 23-2 and 23-3.

Each of first ends 25-1, 25-2 and 25-3 is located in close proximity to front edge 17. Together, first ends 25-1, 25-2 and 25-3 define a reactive area 29 for test sensor 11, reactive area 29 being represented generally within the area bounded by the dashed line in FIG. 1. Reactive area 29 serves as the region on test strip 11 where a test sample (e.g., a blood sample) is applied which, in turn, generates a measurable electrochemical reaction.

Each of second ends 27-1, 27-2 and 27-3 is located, along back edge 19 of substrate 13 in a spaced apart relationship. Configured as such, second ends 27-1, 27-2 and 27-3 are disposed in a manner suitable for connection with corresponding conductors which are housed within the test port of the compatible test meter 12.

An enzyme 30-1 which produces an electrical reaction when exposed to a particular analyte (e.g., glucose) is applied to first end 25-2 of working electrode 23-2 (i.e., within reactive area 29). Similarly, an enzyme 30-2 which produces an electrical reaction when exposed to a particular analyte (e.g., glucose) is applied to first end 25-3 of trigger electrode 23-3 (i.e., within reactive area 29) for reasons to become apparent below.

It should be noted that an optional mesh layer (not shown) may be disposed over first ends 25-1, 25-2 and 25-3 to facilitate in the spreading (i.e., wicking) of a test sample adequately across reactive area 29. In this manner, such a mesh layer would assist in ensuring that an adequate amount of the test sample reacts with enzymes 30-1 and 30-2 in order for sensor 11 to operate accurately. In addition, a layer of insulated material (not shown) may cover a portion of electrodes 23-1, 23-2 and 23-3 to protect test sensor 11 from potentially harmful external conditions (e.g., moisture).

Test strip 11 is additionally provided with a compensation electrode 31 for use in for correcting test result inaccuracies which are the result of variances in manufacturing. As will be described further below, compensation electrode 31 can be used to adjust (i.e., correct) the value of the working current prior to its measurement by the test meter 12. Because compensation electrode 31 can be used to directly adjust the value of the working current prior to its measurement by the test meter 12, compensation electrode 31 is defined herein as providing analog means for correcting test result inaccuracies. To the contrary, conventional calibration means corrects for the inaccuracies of test results in a digital manner (i.e., by measuring the working current and, in a subsequent step, utilizing calibration information to digitally convert the inaccurate working current value to its proper value using a mathematical formula). As can be appreciated, the ability of test strip 11 to correct for test result inaccuracies in an analog manner (i.e., prior to its measurement by a meter) renders the above-described glucose measurement system less costly and easier to use than conventional digital testing means, and accordingly, serves as a principal novel feature of the present invention.

Compensation electrode 31 preferably includes a first end 33 and a second end 35. First end 33 is conductively coupled to working electrode 23-2 at a location between first end 25-2 and second end 27-2. Second end 35 is located along back edge 19 of substrate in close proximity to second end 27-2 of working electrode 23-2.

Compensation electrode 31 is provided with means for readily altering its resistance. Specifically, compensation electrode 31 includes a resistive ladder 37. Resistive ladder 37 is represented herein as a network of resistive conductors that are arranged in a ladder-type configuration. Specifically, resistive ladder 37 is shaped to include a pair of elongated, parallel side rails 39 and a plurality of transversely extending cross-members, or rungs, 41. However, it is to be understood that resistive ladder 37 is not limited to this particular configuration. Rather, resistive ladder 37 could be configured into a wide variety of different patterns (e.g., a grid with any conceivable combination of side rails and rungs) without departing from the spirit of the present invention.

Preferably, compensation electrode 31 includes a bottom layer which is constructed out of a carbon-based material. Resistive ladder 37 is preferably formed by depositing a top layer of gold over said bottom layer. Ladder 37 is constructed out of gold to allow for its etching during an ablation step which will be described further in detail below. However, it should be noted resistive ladder 37 is not limited to being constructed out of gold. Rather, it is to understood that resistive ladder 37 could be constructed out of any conductive material that can be readily ablated without departing from the spirit of the present invention.

Upon completion of the manufacture of test strip 11, resistive ladder 37 provides compensation electrode 31 with a particular resistance. However, it is to be understood that resistive ladder 37 can be customized (i.e., structurally altered) to adjust the resistance of compensation electrode 31. Specifically, after completion of its initial manufacture, an ablation process can be undertaken to cut selected rungs 41 and/or portions of certain side rails 39. As can be appreciated, the ablation of portions of resistive ladder 37 alters the path through which a current travels along compensation electrode 31. This alteration of the current path directly changes the resistance of compensation electrode 31 which, in turn, can be used to adjust (i.e., correct) the working current to its true value prior to its measurement by test monitor 12.

As an example, if one were to sever a portion of either side rail 39 at a location between successive rungs 41, the length of the path which a current would be required to travel along compensation electrode 31 would increase. This increase in the current path would, in turn, increase the overall resistance of compensation electrode 31.

It should be noted that compensation electrode 31 is not limited to the use of a resistive ladder 37 to alter its resistance. Rather, it is to be understood that compensation electrode 31 could be constructed with any conventional means for adjusting its resistance without departing from the spirit of the present invention. For example, rather than modifying the resistance of compensation electrode 31 through the ablation of selected portions of its resistive ladder 37, conductive material could be added (e.g., smeared) onto compensation electrode 31 to alter its resistance.

In addition, although not shown herein, it is to be understood that working electrode 23-2 could similarly be provided with a resistive ladder. In this manner, the resistance value of working electrode 23-2 and/or compensation electrode 31 could be modified (e.g., through an ablation process) in order to correct the value of the working current which is measured by the analyte test meter 12 without departing from the spirit of the present invention.

Test sensor 11 can be used in the following manner to perform an assay. It should be noted that, for simplicity purposes only, test sensor 11 will be described herein for use in calculating the concentration of glucose in a blood sample. However, it is to be understood that test sensor 11 is not limited for use in calculating the concentration of glucose in a blood sample. Rather, test sensor 11 could be used to measure the concentration of alternate types of analytes (other than glucose) in alternate types of test samples (other than a blood sample) without departing from the spirit of the present invention.

In order to commence an assay, test sensor 11 is inserted into the test port of a compatible blood glucose meter 12

(also referred to herein as blood glucose monitor 12) such that second ends 27-1, 27-2 and 27-3 (as well as second end 35 of compensation electrode 31) are drawn into contact with corresponding conductors 44-1, 44-2 and 44-3, respectively, which are housed within the test port, thereby establishing a direct electrical connection between test sensor 11 and test meter 12. As such, with test sensor 11 disposed into the test port, an electrical circuit is effectively created between test sensor 11 and the electronics for test meter 12. A simplified schematic representation of the electrical circuit established between sensor 11 and meter 12 is shown in FIG. 2 and identified generally by reference numeral 43.

Circuit 43 remains effectively open between first ends 25-1 and 25-2 of electrodes 23-1 and 23-2, respectively, until a blood sample is applied onto the reactive area 29 of test sensor 11. Due to the conductive nature of blood, an adequate blood sample serves to create a conductive path between first ends 25-1 and 25-2, the resistance of the blood sample being represented as $R_{blood}$ in FIG. 2. Furthermore, it is to be understood that the conductive nature of each electrode in test sensor 11 inherently provides it with a resistance, the resistance of reference electrode 23-1 being represented as $R_{ref}$ in FIG. 2, the resistance of working electrode 23-2 being represented as $R_{working}$ in FIG. 2, and the resistance of compensation electrode 31 being represented as $R_{compensation}$ in FIG. 2.

The application of an adequate blood sample onto reactive area 29 creates an electrochemical reaction between enzyme 30-2 provided on first end 25-3 of trigger electrode 23-3 and glucose molecules present in the sample (trigger 23-3 not being shown in circuit 43). The electrochemical reaction generates a current which travels along trigger electrode 23-3 and is detected by test meter 12. In response to the detection of an adequate blood sample, a voltage source V housed within test meter 12 applies a voltage (e.g., 200 mv) across second ends 27-1 and 27-2 of electrodes 23-1 and 23-2, respectively. In addition, test meter 12 connects second end 35 of compensation electrode 31 to second end 27-2 of working electrode 23-2, as seen most clearly in FIG. 2.

The application of the blood sample onto enzyme 30-1 similarly creates an electrical reaction. In response to said reaction, an uncompensated, or raw, working current $i_{working}$ is produced at the first end 25-2 of working electrode 23-2, the value of the uncompensated working current $i_{working}$ being proportional to the concentration of glucose in the blood sample.

As noted above, under ideal manufacturing conditions, uncompensated working current $i_{working}$ should be a particular value when a known test sample is utilized. However, manufacturing variances between batches of test sensors often create inaccuracies in the value of the working current generated upon the application of a sample. Accordingly, it is to be understood that compensation electrode 31 can be used to correct the inaccurate working current value to its true, or accurate, value in an analog manner.

Specifically, the uncompensated working current $i_{working}$ generated at first end 25-2 travels along working electrode 23-2 towards second end 27-2. However, at first end 33 of compensation electrode 31, the uncompensated working current $i_{working}$ splits between compensation electrode 31 and the remainder of working electrode 23-2. Specifically, a compensated, or corrected, working current $i_{correct}$ travels along working electrode 23-2 towards second end 27-2 and a shunted current $i_{shunt}$ travels along the compensation electrode 31, the sum of the compensated working current $i_{correct}$ and the shunted current $i_{shunt}$ equaling the value of the uncompensated working current $i_{working}$.

As can be appreciated, the values of the compensated working current $i_{correct}$ and the shunted current $i_{shunt}$ are inversely proportional to the working electrode resistance $R_{working}$ and the compensation electrode resistance $R_{compensation}$, respectively. In this manner, the value of the compensated working current $i_{correct}$ can be readily adjusted to its proper value in an analog manner by changing the compensation electrode resistance $R_{compensation}$ to a particular value (e.g., through the ablation of portions of resistive ladder 37).

A current detection device D provided within meter 12 is connected to second end 27-2 of working electrode 23-2 and measures the value of the compensated working current $i_{correct}$. The microprocessor for meter 12, which is connected to current detection device D, correlates (e.g., using a scaling factor) the compensated working current $i_{correct}$ into an accurate numerical glucose concentration value which is provided on the monitor's display for the patient to observe and which is stored into the meter's memory device.

As noted above, test strip 11 can be used to adjust the value of the uncompensated working current $i_{working}$ to a compensated, or true, working current value $i_{correct}$ through the use of compensation electrode 31. Used in this manner, test strip 11 eliminates the need for the digital calibration of blood glucose meter 12 prior to performing an assay, which is a principal object of the present invention.

Preferably, test sensor 11 is manufactured in the following manner when to be used as described above. A plurality of test sensors 11 are manufactured as part of a common batch. The batch of test sensors 11 is then tested to determine whether one or more common variances in manufacturing (e.g., the size of electrodes 23-1, 23-2 and 23-3 or the amount of enzyme 30-1 deposited working electrode 23-2) compromised the accuracy of each test sensor 11 within this particular batch. Specifically, a limited sampling of the test strips 11 from this batch is tested for accuracy using a blood sample of a known glucose level (i.e., a control solution).

The adjusted working current $i_{correct}$ measured from these test strips 11 is then compared to its target (i.e., correct) working current value. If the measured working current $i_{correct}$ deviates from this target value, the manufacturer can determine that variances compromised the accuracy of each test strip 11 within that batch. The manufacturer then calculates the value by which the resistance of compensation electrode 31 should be changed (i.e., increased or decreased) in order to alter the adjusted working current $i_{correct}$ to match the target value. The manufacturer then determines which portions of resistive ladder 37 require ablation in order to produce this calculated resistance for compensation electrode 31.

Having determined the particular pattern for resistive ladder 37 that is required to convert compensation electrode 31 to its desired resistance, each remaining test strip 11 in the batch is modified accordingly. Specifically, selected portions of the resistive ladder 37 for each remaining test strip 11 are commonly ablated (e.g., using a laser) to configure resistive ladder 37 into its proper pattern. In this manner, each remaining test strip 11 is adjusted, or corrected, to provide accurate test results, which is highly desirable. The corrected test strips 11 can then be used to acquire accurate glucose readings without the need to perform a digital calibration of blood glucose monitor 12 before testing.

Although compensation electrode 31 can be used to correct in an analog manner for inaccuracies introduced during the manufacture of test strip 11, it is to be understood that compensation electrode 31 could alternatively be used to compensate for manufacturing variances in a digital manner without departing from the spirit of the present invention. As will be described further below, in order to compensate for manufacturing variances in a digital manner, test strip 11 must be used in conjunction with a blood glucose meter 45 which includes switching means.

Figure 3A:
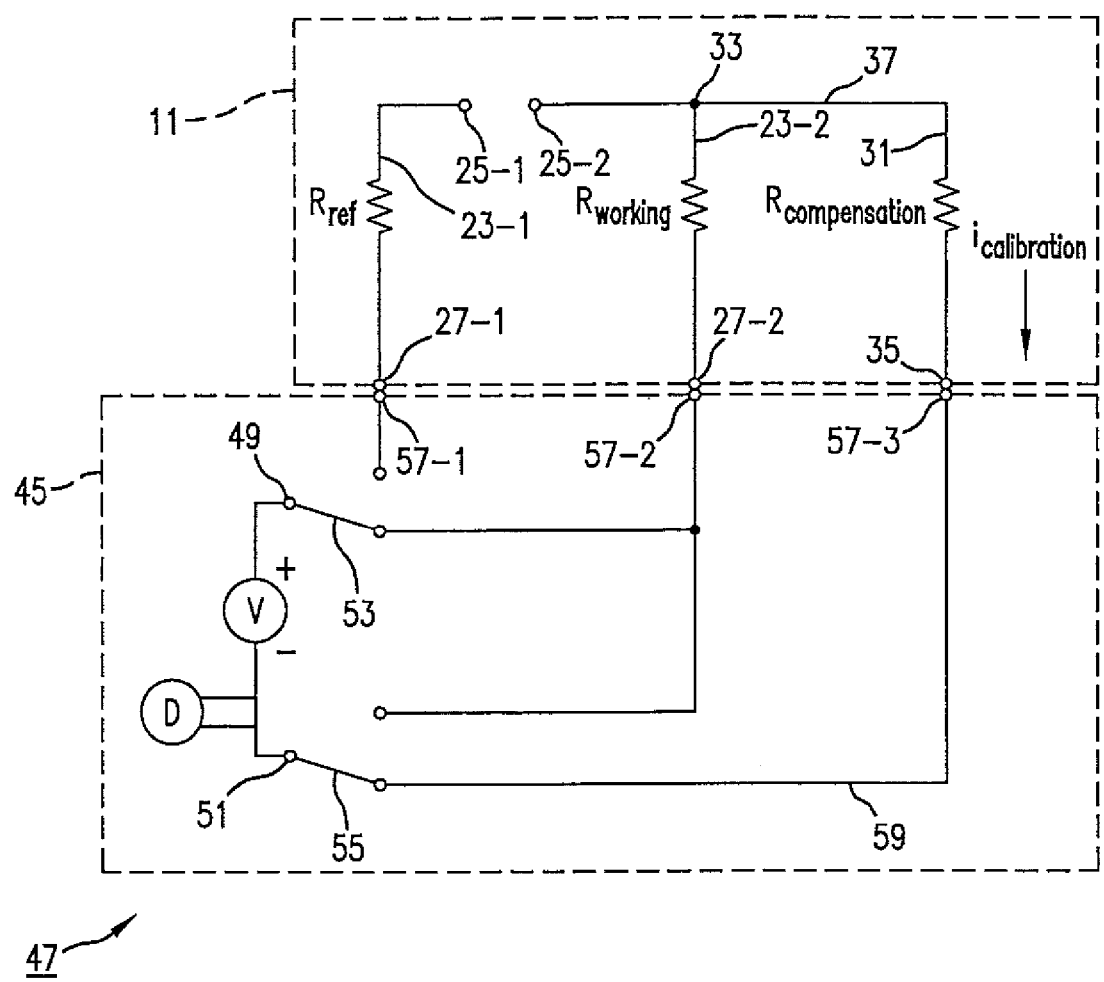
FIG. 3(a) is a simplified electrical schematic of the test sensor shown in FIG. 1 installed into a second embodiment of a compatible blood glucose meter, the test sensor and the meter together operating to measure the concentration of a particular analyte in a test sample, wherein inaccuracies in the test results which are caused from variances in manufacturing the test strip are compensated for in a digital manner, the schematic being shown with each of a pair of switches disposed in its first position.
Figure 3B:
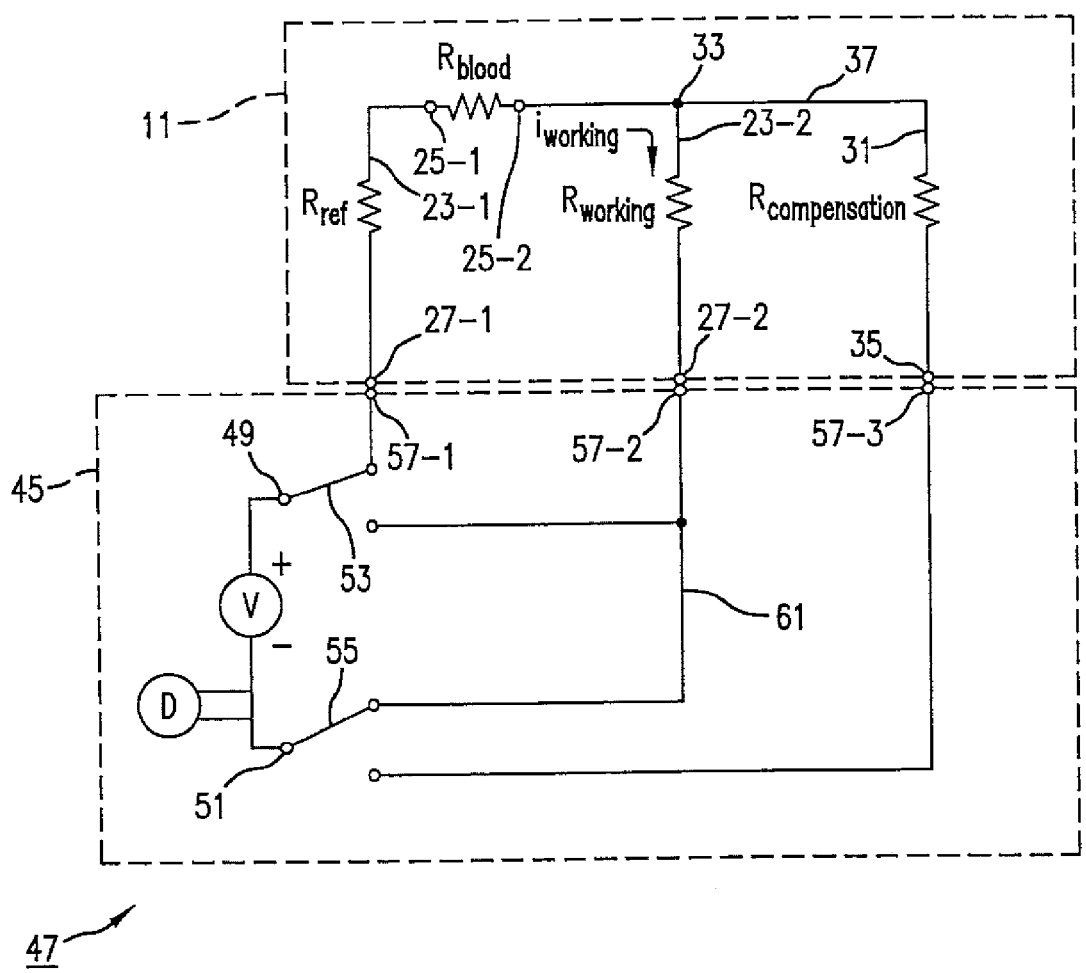
FIG. 3(b) is the simplified electrical schematic shown in FIG. 3(a) with each of the pair of switches disposed in its second position and with an adequate test sample applied onto the reactive area of the test strip.

Referring now to FIGS. 3(a)-(b), there are shown schematic representations of an electrical circuit which is established when test sensor 11 is properly inserted into meter 45, the circuit being identified generally by reference numeral 47.

Blood glucose meter 45 includes a voltage source V of a constant value (e.g., 200 mv) which includes a first terminal 49 and a second terminal 51. First terminal 49 of voltage source V is connected to either of second ends 27-1 and 27-2 of electrodes 23-1 and 23-2, respectively, by means of a single-pole, double throw switch 53. Similarly, second terminal 51 of voltage source V is connected to either of second ends 27-2 and 35 by means of a single-pole, double throw switch 55. Furthermore, a current detection device D is provided within meter 45 and is connected to second terminal 51. As will be described further below, switches 53 and 55 enable test strip 11 to: (1) provide meter 45 with calibration information in a digital manner and (2) allow for the calculation of the concentration of a particular analyte in a test sample using said calibration information.

Test sensor 11 can be used in conjunction with blood glucose meter 45 to perform an assay. Specifically, in order to commence an assay, test sensor 11 is inserted into the test port of compatible blood glucose meter 45 (also referred to herein as blood glucose monitor 45) such that second ends 27-1, 27-2 and 35 of test strip 11 are drawn into direct electrical contact with corresponding conductors 57-1, 57-2 and 57-3, respectively, which are housed within the test port, thereby establishing a direct electrical connection between test sensor 11 and meter 45. As such, with test sensor 11 disposed into the test port, an electrical circuit 47 is effectively created between test sensor 11 and the electronics for test meter 45.

As seen most clearly in FIG. 3(a), upon the initial insertion of test sensor 11 into meter 45, each of switches 53 and 55 is disposed in a first position. Specifically, switch 53 is disposed such that terminal 49 is drawn into connection with conductor 57-2. Similarly, switch 55 is disposed such that terminal 51 is drawn into connection with conductor 57-3. With switches 53 and 55 disposed in their first position, a closed loop 59 is defined within circuit 47 amongst working electrode 23-2, compensation electrode 31 and voltage source V.

The application of voltage from voltage source V into closed loop 59 creates a calibration current $i_{calibration}$ along compensation electrode 31. The calibration current $i_{calibration}$ which travels along compensation electrode 31 is measured by current measuring device D and, in turn, is used to calibrate meter 45 prior to performing an assay using test strip 11. Specifically, the microprocessor (not shown) for meter 45 (which is connected to device D) recognizes the measured calibration current $i_{calibration}$ as a particular code which is then used to digitally calibrate test meter 12.

In this manner, compensation electrode 31 provides test strip 11 with on-board digital calibration information. Unlike most conventional blood glucose monitoring systems which utilize digital calibration methods, test strip 11 provides its calibration information directly on the test strip itself rather than on a separate calibration strip. As a result, the present system is easier to use and less expensive to manufacture than conventional digital calibration means.

It should be noted that the calibration information provided from compensation electrode 31 (in the form of a particular calibration current) can be altered simply by modifying the resistance of compensation electrode 31. In fact, increasing the resistance of compensation electrode $R_{compensation}$ serves to decrease the value of the calibration current $i_{calibration}$ and vice versa. As noted above, modification of the resistance of compensation electrode 31 is readily accomplished by ablating selected portions of resistive ladder 37 (e.g., using a laser). As can be appreciated, the relatively large (i.e., potentially infinite) number of possible resistance values for compensation electrode $R_{compensation}$ can be used to generate a relatively large number of calibration currents. As a result, it is to be understood that test strip 11 is designed to accommodate a large (i.e., potentially infinite) number of possible digital calibration codes, which is highly desirable.

With meter 45 having been digitally calibrated in the manner as described above, the microprocessor for meter 45 moves each of switches 53 and 55 to a second position. Specifically, as seen most clearly in FIG. 3(b), switch 53 is disposed such that terminal 49 is drawn into connection with conductor 57-1. Similarly, switch 55 is disposed such that terminal 51 is drawn into connection with conductor 57-2.

At the same time, the user is requested to apply a blood sample onto the reactive area 29 of test sensor 11. Due to the conductive nature of blood, an adequate blood sample serves to create a conductive path between first ends 25-1 and 25-2, the resistance of the blood sample being represented as $R_{blood}$ in FIG. 3(b). Accordingly, with switches 53 and 55 disposed in their second positions, a closed loop 61 is defined within circuit 47 amongst reference electrode 23-1, working electrode 23-2 and voltage source V.

The application of the blood sample onto enzyme 30-1 creates an electrical reaction at first end 25-2 of working electrode 23-2. In response to said reaction, an uncompensated, or raw, working current $i_{working}$ is produced at the first end 25-2 of working electrode 23-2, the value of the uncompensated working current $i_{working}$ being directly related to the concentration of glucose in the blood sample. The uncompensated working current $i_{working}$ generated at first end 25-2 travels along the entire length of working electrode 23-2 and ultimately is measured by current detection device D. The microprocessor for meter 12, which has already received the calibration information for test strip 11 via compensation electrode 31, digitally correlates (e.g., using a scaling factor) the uncompensated working current $i_{working}$ into a compensated, or true, working current value. This compensated working current value is then utilized by meter 12 to calculate the standard glucose concentration value for the sample, the glucose concentration value being provided on the monitor's display for the patient to observe and stored into the meters memory device.

Preferably, test sensor 11 is manufactured in the following manner when to be used as part of a digital calibration system. A plurality of test sensors 11 are manufactured as part of a common batch. The batch of test sensors 11 is then tested to determine whether a common variance in manufacturing (e.g., the size of electrodes 23-1, 23-2 and 23-3 or the amount of enzyme 30-1 deposited working electrode 23-2) compromised the accuracy of the test sensors 11 within this particular batch. Specifically, with switches 53 and 55 disposed in their second position (as represented in FIG. 3(b)), a limited sampling of the test strips 11 from this batch is tested for accuracy using a blood sample of a known glucose level (i.e., a control solution).

The working current measured from these test strips 11 is then compared to its target (i.e., correct) value. If the measured working current deviates from this target value, the manufacturer can determine that variances compromised the accuracy of each test strip 11 within that batch. Based on the results of the tests, the manufacturer then assigns a particular value calibration current $i_{current}$ to test strip 11, said calibration current $i_{current}$ serving as a particular calibration code for the test strip 11. The manufacturer then calculates the value of the compensation resistance $R_{compensation}$ which would produce this desired calibration current $i_{current}$ for test strip 11 and, in turn, determines which portions of resistive ladder 37 require ablation in order to produce the desired resistance for compensation electrode 31.

Having determined the particular pattern for resistive ladder 37 that is required to convert compensation electrode 31 to its desired resistance, each remaining test strip 11 in the batch is modified accordingly. Specifically, selected portions of the resistive ladder 37 for each remaining test strip 11 are commonly ablated (e.g., using a laser) to configure resistive ladder 37 into its proper pattern. In this manner, each remaining test strip 11 in the batch is provided with a specific on-board digital calibration code, which is highly desirable.

Figure 4:
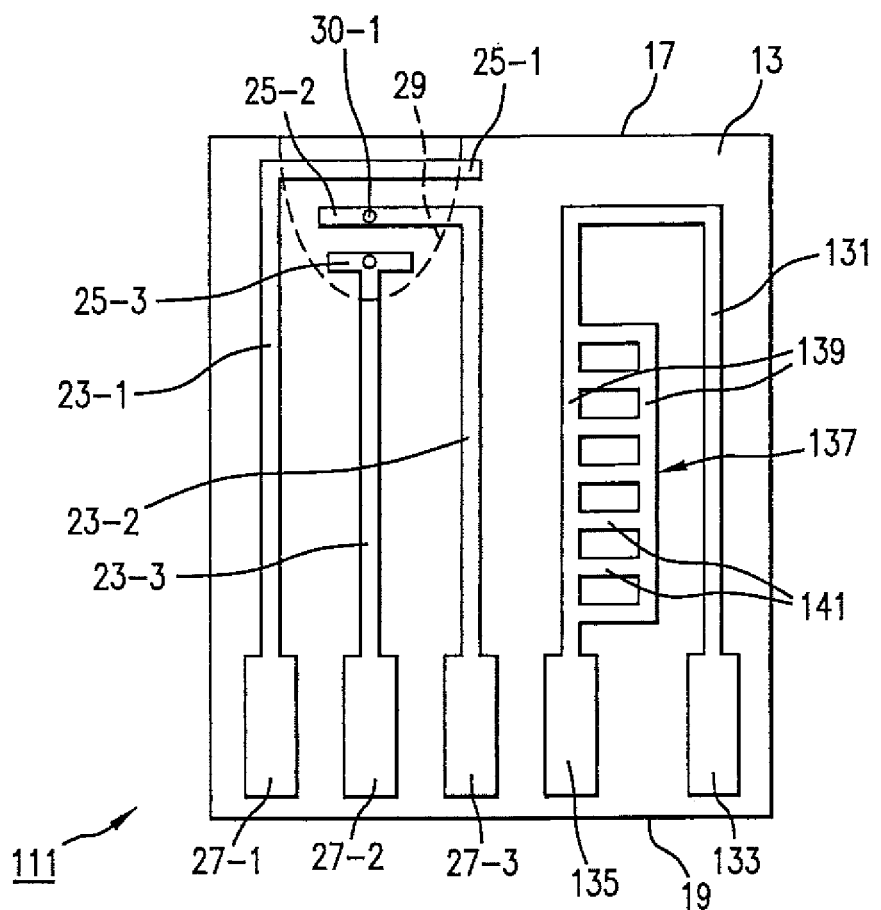
FIG. 4 is a top plan view of a second embodiment of a test sensor constructed according to the teachings of the present invention.

It is to be understood that the particular construction of test strip 11 could be modified without departing from the spirit of the present invention. For example, referring now to FIG. 4, there is shown a second embodiment of a test strip constructed according to the teachings of the present invention, the test strip being identified by reference numeral 111. As will be described further below, test strip 111 is similar to test strip 11 in that test strip 111 includes on-board means for performing digital calibration.

Test strip 111 is identical in construction to test strip 11 in all respects with one notable exception. Specifically, test strip 111 includes a compensation electrode 131 of a slightly different design than compensation electrode 31 in test strip 11.

Compensation electrode 131 is similar in construction to compensation electrode 31 in that compensation electrode 131 includes a first end 133, a second end 135 and a resistive ladder 137 formed thereinto along a portion of its length, resistive ladder 137 being shaped to include a pair of elongated, parallel side rails 139 and a plurality of transversely extending cross-members, or rungs, 141.

Compensation electrode 131 differs from compensation electrode 31 in that first end 133 of compensation electrode 131 is located along back edge 19 of substrate 13 in close proximity to second end 135. As such, compensation electrode 131 is spaced away from working electrode 23-2, whereas compensation electrode 31 is disposed in connection with working electrode 23-2. In this manner, compensation electrode 131 is electrically insulated from the remainder of electrodes 23-1, 23-2 and 23-3.

Accordingly, it is to be understood that the sole function of compensation electrode 131 is to provide digital calibration information for test strip 111. The digital calibration information is represented in the form of a particular current which is inversely proportional to the resistance of compensation electrode 131, this current being provided upon applying a voltage across first end 133 and second end 135. In this manner, by changing the resistance of resistive ladder 137, the manufacturer can modify the value of the calibration current which is utilized by a corresponding meter for calibration purposes. After digital calibration of the meter has been performed using compensation electrode 131, electrodes 23-1, 23-2 and 23-3 are utilized to perform an assay.

The embodiments shown in the present invention are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A method of making a plurality of calibration-adjusted sensors, the method comprising:
    applying a known voltage to an electrode pair of a first sensor from a batch of sensors to produce a working current through the electrode pair of the first sensor;
    measuring the working current of the first sensor in the presence of a control sample;
    determining the working current of the first sensor;
    wherein when the working current of the first sensor is not the same as a target working current, modifying a resistance of an electrode pair of a second sensor from the batch of sensors;
    measuring a working current of the second sensor in the presence of a control sample to confirm that when the known voltage is applied to the electrode pair of the second sensor, the second sensor will have a working current that is the same as the target working current.

2. The method according to claim 1, further comprising:
    modifying the resistance of an electrode pair of all the sensors in the batch of sensor such that all the sensors will have a working current that is the same as the second sensor.

3. The method according to claim 1, wherein each sensor of the batch of sensors comprises:
    a first substrate having a working electrode thereon; and
    an insulation layer over the first substrate.

4. The method according to claim 1, wherein modifying the resistance of the electrode pair of the second sensor comprises modifying an electrode configuration.

5. The method according to claim 1, wherein an electrode of the second sensor is a working electrode.

6. The method according to claim 1, wherein an electrode of the second sensor is a compensation electrode.

* * * * *